United States Patent [19]

Broadbent

[11] Patent Number: 4,595,679

[45] Date of Patent: Jun. 17, 1986

[54] INSECTICIDAL COMPOSITIONS UTILIZING 2-PYRROLIDONES HAVING ENHANCED INSECT KNOCKDOWN CHARACTERISTICS

[75] Inventor: David J. Broadbent, Racine County, Wis.

[73] Assignee: S. C. Johnson & Son, Inc., Racine, Wis.

[21] Appl. No.: 674,399

[22] Filed: Nov. 23, 1984

[51] Int. Cl.$^4$ .................. A01N 47/10; A01N 53/00; A01N 57/00; A01N 65/00

[52] U.S. Cl. .............................. 514/67; 514/65; 514/86; 514/89; 514/120; 514/122; 514/136; 514/421; 514/465; 514/479; 514/521; 514/531; 514/937; 514/938

[58] Field of Search .............. 424/186, 187, 300, 225, 424/260, 218; 514/86, 122, 67, 65, 479, 937, 938

[56] References Cited

U.S. PATENT DOCUMENTS

| | | | |
|---|---|---|---|
| 3,894,149 | 7/1975 | Mast | 424/288 |
| 3,903,273 | 9/1975 | Mast | 424/225 |
| 4,331,682 | 5/1982 | Ackermann et al. | 424/305 |
| 4,377,593 | 3/1983 | Ackermann et al. | 424/282 |
| 4,380,537 | 4/1983 | Monroe | 424/216 |

FOREIGN PATENT DOCUMENTS

| | | | |
|---|---|---|---|
| 700886 | 3/1980 | Romania . | |
| 695393 | 7/1969 | South Africa . | |
| 1415514 | 11/1975 | United Kingdom | 424/187 |

OTHER PUBLICATIONS

The Merck Index, 9th Ed. (1976), #7804.
Harvey et al., Advanced Chemical Ser., vol. 86, pp. 81–90, 1969.
Hartley et al., Physical Principles of Pesticide Behavior, vol. 2, pp. 658–676, 1980.

*Primary Examiner*—Allen J. Robinson

[57] ABSTRACT

A liquid insecticidal composition having enhanced insect knockdown comprising an active insecticide, a liquid medium for emulsifying, dispersing, or solubilizing the insecticide, and at least one of N-vinyl 2-pyrrolidone, N-methyl 2-pyrrolidone, and 2-pyrrolidone. The amphiphilic solvency characteristics of the 2-pyrrolidones increases the penetration of the insecticide into the body of the insect to provide enhanced insect knockdown.

5 Claims, No Drawings

INSECTICIDAL COMPOSITIONS UTILIZING 2-PYRROLIDONES HAVING ENHANCED INSECT KNOCKDOWN CHARACTERISTICS

FIELD OF INVENTION

This invention relates to improved insecticides. More particularly, the present invention relates to improved insecticidal compositions comprising an active insecticidal agent, such as synergized pyrethrins, carried in a liquid medium comprising N-vinyl 2-pyrrolidone, N-methyl 2-pyrrolidone, or 2-pyrrolidone. The presence of the select 2-pyrrolidone carrier is believed to increase the penetration of the active insecticidal agent into the body of an insect to provide enhanced insect knockdown.

BACKGROUND AND PRIOR ART

Insecticides are extensively employed to kill household insects such as the common housefly, cockroaches, and the like. Insecticides which have acquired common usage are conventionally utilized, often from an aerosol container, in the form of aqueous emulsions, aqueous colloidal suspensions, aqueous solutions, or from an organic solvent medium. Normally the use of an aqueous medium is the preferred form from the standpoint of economics and ecological considerations. However, many of the more effective active insecticidal agents are difficultly soluble or not soluble at all in water, and at times cannot be conveniently emulsified in an aqueous medium—at least not to provide a transparent emulsion or an emulsion free from staining or other undesired characteristics including low activity. This has required, therefore, the use of organic solvents as the carrier for the insecticide in certain applications and with certain active insecticidal agents in order to obtain solubility and the essential activity. With other insecticides, because of their insolubility in water and in the commonly employed organic solvents, it has been customary to employ the insecticides as a powder.

More recently, in an effort to provide insecticidal compositions wherein even the most difficultly soluble insecticidal agents are carried in a solvent medium, organic materials having increased solvency power have been selected, included solvents having amphiphilic character, i.e., solvents having both hydrophilic and lipophilic properties; such as 2-pyrrolidone and N-methyl 2-pyrrolidone. In the insecticidal compositions utilizing such solvents, the amphiphilic solvents have been used solely as a solvent for the active insecticidal agent, which materials were primarily used as powders because of their limited solubility. Thus, the amphiphilic solvents have been used primarily with insecticidal agents which were not capable of being solubilized in the more conventional solvent. Note, for example, the disclosure in the Republic of South Africa Application for Pat. No. 695,393 filed July 28, 1969. There is no recognition in the prior art that the aforesaid amphiphilic solvents would provide a beneficial effect such as enhanced activity to the insecticidal formulation.

It is also recognized that in formulating an insecticide, particularly those having household usage such as the Raid ® products manufactured by S. C. Johnson & Son, Inc., Racine, Wis., the assignee of the present application, it is essential not only to provide a formulation providing a high kill of the insects, but it is also essential to have rapid knockdown of the insects. Knockdown, as the term is used herein, is the characteristic of the insecticide whereby the insect, if a flying insect such as a common housefly, is knocked out of the air or, if a crawling insect, is caused to lie dormant giving the appearance of death to the insects, even if not dead. Rapid knockdown is essential in such insecticides since the average user equates the effectiveness of the insecticide with the falling out of the air of a flying insect, such as the common housefly, or with the paralyzing of an insect, if a crawling insect such as the common cockroach, even though the insect, although not knocked down or paralyzed, may die later. To obtain the desired knockdown, it has been necessary to utilize the active insecticidal agent in larger amounts than necessary to obtain a kill. This is undesirable from the standpoint of cost and also from the standpoint of the ecology.

Although the knockdown phenomenon, and the need for knockdown, has long been known, the solutions advanced in the art to obtain rapid knockdown have centered around the use of synergistic combinations of insecticides such as the pyrethrins in combination with piperonyl butoxide wherein one component contributes high kill and the other rapid knockdown, or merely increasing the amount of active ingredient in the formulation. Neither solution is fully satisfactory from the standpoint of, inter alia, cost and the ecology. Accordingly, there is and has been a need for an effective means of providing knockdown power in an insecticidal composition without using large amounts of the insecticidal agent, or combinations of expensive insecticidal agents.

OBJECTS AND GENERAL DESCRIPTION OF THE INVENTION

A primary object of the present invention is to provide an insecticidal composition having increased knockdown power for a given level of active insecticidal agent.

It is another object of the present invention to provide an insecticidal composition in the form of an aqueous, transparent emulsion that is capable of providing knockdown performance at least the equivalent of a conventional solvent-based formulation.

It is another object of the present invention to provide an insecticidal composition which will deliver a greater knockdown performance than that demonstrated by a conventional formulation using the same amount of insecticidal agent.

It is another object of the present invention to provide an insecticidal composition effective against flying insects such as the common housefly and against crawling insects such as the cockroach having knockdown performance for both the flying and crawling insects equivalent to the knockdown performance of separately formulated insecticides for each type of insect.

It is another object of this invention to provide an insecticidal composition which has the knockdown performance while using a lower level of active insecticidal agent equivalent to that of a conventional insecticidal formulation which uses a higher level of insecticidal agent.

These and other objects of the invention will be apparent from the following more detailed description.

The objects of the present invention are accomplished by utilizing in an insecticidal formulation N-vinyl 2-pyrrolidone, N-methyl 2-pyrrolidone, or 2-pyrrolidone as a carrier for an active insecticidal agent. It has been determined that insecticidal formulations including the aforesaid organic materials, particularly the N-vinyl 2-pyrrolidone, have greatly enhanced knockdown power in comparison to a conventional formulation not using such carrier although utilizing an equivalent amount of the active insecticidal agent. The improved knockdown characteristics are particularly effective when using as the active insecticidal agent a synergistic combination of pyrethrins and piperonyl butoxide, or Baygon. Moreover, N-vinyl 2-pyrrolidone is particularly effective, even in comparison to N-methyl 2-pyrrolidone and 2-pyrrolidone, with respect to the common household insects such as the housefly and the cockroach.

To understand the reasons for the improved knockdown, the nature of the formulations and the effect thereof on insects have been investigated. The investigation establishes that the improved knockdown power of the presently described formulations is a result of the improved penetration of the active insecticidal agent into the body of the insect, apparently as a result of being carried by the aforesaid 2-pyrrolidones and the amphiphilic solvency characteristics of such components. The explanation of the improved knockdown power, developed after the discovery of this unexpected phenomenon, is consistent with the anatomical make-up of the insect. Thus, the insect cuticle is essentially a multi-laminated barrier of lipophilic and hydrophilic layers which regulate the movement of water, ions, and other substances between the insect's internal tissues and the exterior environment. The cuticle not only covers all of the insect's external body surface, but also extends inward into the fore- and hind-guts, and the tracheal system. The cuticle is composed of three main layers: an inner endocuticle that is covered by an outer exocuticle which is, in turn, covered by a superficial epicuticle. The endocuticle which is composed mainly of protein and chitin (a polysaccharide of N-acetylglucosamine units) is relatively soft and elastic, and is the main component of the cuticle in larvae and other soft-body insects such as the housefly. Chitin is present as long crystalline microfibrils, arranged heterogeneously in a hydrophilic protein matrix. The exocuticle is the more important component in hard-bodied insects such as the cockroach, but may be present as a very thin layer in many larvae and in the hard parts of soft-bodied insects. Unlike the endocuticle, the exocuticle is a homogenous matrix of chitin and quinone-tanned proteins which provide to that cuticle the typical rigid structure, or sclerotization. The matrix is hydrophilic in property, but somewhat less permeable than the endocuticle. The lipoidal epicuticle is the main barrier which prevents the penetration of insecticides. The epicuticle can vary in thickness in different species of insects from about 0.04 to 4.0 $\mu$m, and consists of an inner layer of tanned-lipoproteins, covered with an outer layer of cuticulin grease or wax. The outermost cuticulin layer also varies in thickness and composition between species, but generally contains alkanes, and esters of saturated and unsaturated n-alcohols and acids, in the range of $C_{25}$ to $C_{31}$. The entire cuticle is transversed by a network of fine-branched pores that emanate from the epidermal cells and pass outwards to end at various levels in the epicuticle. These pore canals are 10 to 100 $\mu$m in diameter and are of two general types, those that are primarily lipophilic which serve to replenish the cuticulin wax, and those that are primarily hydrophilic which house a nerve filament for a chemoreceptor.

The major route by which a contact insecticide penetrates into the insect is not completely understood. The complex structure of the cuticle and its variations within and between insects creates many difficulties when considering penetration of a substance therethrough. Despite these difficulties, certain generalizations are reasonable. It is understandable that the penetration rate of insecticides through the cuticle is positively related to the polarity of the insecticide. With decreasing polarity, molecules penetrate more easily into the lipid-rich epicuticle barrier; but, on the other hand, the higher the polarity the faster they can leave that lipoidal barrier and penetrate into the more polar inner layers of the insect cuticle. There is, therefore, an optimum in polarity at which passing through a lipophilic/hydrophilic barrier is maximal. The speed of penetration, or the partitioning from the apolar epicuticle into the more polar exocuticle and endocuticles is, understandably, favored by increased polarity. The higher the lipopholicity of any component above the optimum, the more that component will remain in the waxy cuticular phase and be retarded from further penetration. If, however, a toxicant is dissolved in water, a very polar solvent, the toxicant would not be expected to permeate the epicuticle lipids until the water has evaporated, or at the rate determined by its own partition coefficient between water and the outer most layer of the cuticulin wax, which rate is favored by an increased lipopholicity. In general, penetration would be expected to occur more rapidly through thinner non-sclerotized regions of cuticle, such as the intersegmental membranes, sensilla, and chemoreceptors. The cuticular pore and wax canals are likely important routes of entry for both lipophilic and hydrophilic materials. Regardless of the entry route, one can reasonably conclude that conflicting solubility properties are required for rapid penetration through the entire cuticle, so that compounds that offer a compromise between polar and apolar properties are likely to be the most successful bio-transfer agents.

It is not fully understood in insecticide formulations how penetration is affected by the kinetics of the solvent/cuticle interface. A solvent, whether fugitive or persistent, will exert a great influence on the penetration of a dissolved substance. Penetration is promoted by at least three interacting processes that take place at the epicuticle interface. These are (1) surface migration; (2) association with epicuticular lipids, and (3) concentration of the solute. The solvent properties which control these processes are volatility, viscosity, surface tension, and a favorable lipid-water partition coefficient. The rate of penetration across a barrier varies directly with the greater area of interface across which the diffusion occurs. The amount of area over which a given volume of solution will spread is dependent upon lipid solubility, viscosity, and upon its volatility which determines the length of time the solvent can exert its influence before evaporating. The faster a solvent or bio-transfer agent can spread and cover the entire cuticle, the greater the number of entry routes which are interfaced within the least amount of time and, thus, resulting in a faster physiological response such as knockdown. It can be theorized, therefore, that the select 2-pyrrolidone, and particularly the N-vinyl 2-pyrrolidone, which rapidly evaporates introduces the toxicant directly into the cuticulin layers from which diffusion occurs directly into the more polar exocuticle, and essentially by-passes the epicuticle function as a penetration barrier.

In any event, it is evident, based on the experimental studies conducted and a literature search, that the rate of entry into insects of different penetrants will depend on their physio-chemical properties which is determined by the penetrants' affinities to the materials comprising the cuticle. It has been found that the select 2-pyrrolidones noted hereinbefore, i.e., 2-pyrrolidone, N-methyl 2-pyrrolidone, and particularly N-vinyl 2-pyrrolidone; are uniquely qualified for penetrating the housefly, cockroach and other common household insects, and, thus, enhance the knockdown of these insects without detracting from the kill power of the active insecticide toward these insects.

In establishing the superior performance of the insecticidal formulations utilizing the select 2-pyrrolidone carriers and in attempting to define the reason for the superior performance, a series of experiments were carried out. The following is a description of the experimental methods employed, the results obtained, and a brief analysis of the results.

EXPERIMENTAL METHODS (1) Basic Formulation

The select 2-pyrrolidone carriers (experimental carrier) are utilized in the following formulations as partial replacements for either kerosene in a solvent base, or for water in an emulsion system. Insecticide actives in both systems are formulated by weight; whereas the experimental carrier and other liquid components are formulated by volume. An exception is where n-pentane is formulated by weight to replace the gaseous propellent in the aqueous emulsion. All formulations are prepared as liquid concentrates to be atomized by a hand-held air pressurized sprayer.

|  | % Conc. in Product |
|---|---|
| A. Solvent Base System: | |
| Toxicant Intermediate: | |
| Pyrethrins (a.i.), by weight | .05 to 0.8 |
| Piperonyl butoxide, by weight | 1.0 |
| Acetone co-solvent, by volume | balance to 20% |
| Liquid Intermediate: | |
| Pyrrolidone, by volume | 1 to 80 |
| Kerosene (deodorized), by volume | balance to 100% |
| B. "Water-Out" Emulsion, Macro System: | |
| Toxicant Intermediate: | |
| Pyrethrins (a.i.), by weight | 0.2 |
| Piperonyl butoxide, by weight | 1.0 |
| Emulsifier,* by weight | 1.0 |
| Toluene co-solvent, by volume | 5.0 |
| Liquid Intermediate: | |
| Pyrrolidone, by volume | 4 to 16 |
| Water (deionized), by volume | balance to 100% |
| C. "Oil-Out" Emulsion, Macro System: | |
| Toxicant Intermediate: | |
| Pyrethrins (a.i.), by weight | .02 to 1.0 |
| Piperonyl butoxide, by weight | 1.0 |
| Emulsifier,* by weight | 1.1 |
| Isopar-L co-solvent, by volume | 5.0 |
| Liquid Intermediate: | |
| Pyrrolidone, by volume | 1 to 25 |
| Pentane, by weight | 30 |
| Water (deionized), by volume | balance to 100% |
| D. "Oil-Out" Emulsion, Micro System | |
| Toxicant Intermediate: | |
| Pyrethrins (a.i.), by weight | 0.2 to 1.0 |
| Piperonyl butoxide, by weight | 1.0 |
| Emulsifier,* by weight | 1.1 |
| Liquid Intermediate: | |
| Pyrrolidone,** by volume | 1 to 25 |
| Pentane, by weight | 30 |
| Water (deionized), by volume | balance to 100% |

*Emulsifier: 28% Span 80, 72% Tween 80 (HLB-12)
*Emulsifier: 10% Span 80, 90% Stearic Acid ETO Adduct (32589)
**10 to 15% vinyl pyrrolidone forms a transparent emulsion As used herein, a "water-out" emulsion means that the continuous phase of the emulsion is water, i.e., an oil-in-water emulsion; and in an "oil-out" emulsion the continuous phase is an oil, i.e., a water-in-oil emulsion.

(2) Applications

In the experimental work, which also constitute the presently preferred embodiments of the invention, the housefly and German cockroach are used as representative insects having, respectively, a lesser and greater penetration barrier owing to their difference in cuticle composition. The housefly is a soft-bodied insect having a thinner layer of epi- and exocuticle in comparison to the greasy and hard-bodied cockroach. Potentiation is measured by the ability of the select carrier to increase the knockdown performance of synergized pyrethrins when applied at conventional concentration levels.

A. Space Spray Test Method—A Modified Peet-Grady

Approximately 500 houseflies mixed as to sex are allowed several minutes of free flight inside a 216 cu.ft. Peet-Grady chamber. Tests are initiated by atomizing at 45 psi; 1 gram of the experimental formula is discharged into the test chamber through pneumatic-operated port doors. Percent knockdown is measured by the number of "down" flies within the first 15 minutes after treatment. The "down" flies are then transferred to clean CSMA fly cages and fed for 24 hours, after which the percent kill is recorded based on the original number of test flies, and those that are knocked down after 15 minutes. A $KD_{50}$ value in minutes is determined for each formula by probit analysis using the average percent knockdown of four separate tests.

B. Direct Spray Test Method 0.5 or 1.0 gram of the experimental formula is atomized at 10 psi onto 10 insects that are caged in a screened one-half pint cardboard container. The insects are stationed 12 or 18 inches from the hand-held CSMA sprayer. Activity is measured by the number of insects knocked down immediately after treatment, and up to 5 minutes thereafter. A $KD_{50}$ value in minutes is determined for each formula by probit analysis using the average percent knockdown of 5 to 10 replicates.

In the following tables,

| | |
|---|---|
| ACE = | acetone |
| i-PL = | isopar-L |
| KER = | kerosene |
| MEK = | methylethylketone |
| MP = | N—methyl 2-pyrrolidone |
| P = | 2-pyrrolidone |
| PB = | piperonyl butoxide |
| PEN = | pentane |
| PYR = | pyrethrins |
| VP = | N—vinyl 2-pyrrolidone |

Also as used herein, vinyl pyrrolidone means the N-vinyl 2-pyrrolidone; and methyl-pyrrolidone means the N-methyl 2-pyrrolidone.

TABLE 1

Housefly Knockdown of Synergized Pyrethrins in a Water-In-Oil Emulsion by a 0.5 g Direct Spray Application Atomized at 10 psi, 18 inch Distance.

| % Concentration In Formula (w/v) | | | | | | | | % Knockdown | | | | | | | KD50 | Equitoxicity | |
|---|---|---|---|---|---|---|---|---|---|---|---|---|---|---|---|---|---|
| PYR | PB | i-PL | PEN | VP | MP | P | H$_2$O | .25' | .50' | .75' | 1.0' | 1.25' | 1.5' | AVE | Min. | % PYR | Index |
| 0.2 | 1.0 | 5 | 30 | 0 | 0 | 0 | bal | 19 | 29 | 57 | 80 | 91 | 96 | 62.0 | 0.68 | .20 | 1.0 |
| 0.4 | 1.0 | 5 | 30 | 0 | 0 | 0 | bal | 27 | 46 | 60 | 90 | 99 | 100 | 71.4 | 0.59 | .40 | 2.0 |
| 0.8 | 1.0 | 5 | 30 | 0 | 0 | 0 | bal | 45 | 88 | 100 | 100 | 100 | 100 | 88.8 | 0.28 | .80 | 4.0 |
| 0.2 | 1.0 | 5 | 30 | 5 | 0 | 0 | bal | 12 | 23 | 40 | 78 | 87 | 97 | 56.2 | 0.78 | <.20 | <1.0 |
| 0.2 | 1.0 | 5 | 30 | 20 | 0 | 0 | bal | 23 | 35 | 57 | 77 | 91 | 100 | 63.8 | 0.66 | .23 | 1.2 |
| 0.2 | 1.0 | 5 | 30 | 0 | 5 | 0 | bal | 28 | 45 | 75 | 96 | 100 | 100 | 74.0 | 0.56 | .45 | 2.3 |
| 0.2 | 1.0 | 5 | 30 | 0 | 20 | 0 | bal | 28 | 53 | 75 | 93 | 100 | 100 | 74.8 | 0.56 | .45 | 2.3 |
| 0.2 | 1.0 | 5 | 30 | 0 | 0 | 5 | bal | 11 | 28 | 60 | 85 | 92 | 100 | 62.7 | 0.68 | .21 | 1.0 |
| 0.2 | 1.0 | 5 | 30 | 0 | 0 | 20 | bal | 33 | 64 | 77 | 93 | 100 | 100 | 77.8 | 0.50 | .52 | 2.6 |
| 0.2 | 1.0 | 0 | 30 | 5 | 0 | 0 | bal | 33 | 48 | 72 | 89 | 93 | 97 | 71.7 | 0.55 | .42 | 2.1 |
| 0.2 | 1.0 | 0 | 30 | 10 | 0 | 0 | bal | 69 | 94 | 100 | 100 | 100 | 100 | 93.7 | 0.20 | E1.20 | E6.0 |
| 0.2 | 1.0 | 0 | 30 | 15 | 0 | 0 | bal | 44 | 73 | 96 | 100 | 100 | 100 | 85.5 | 0.33 | .72 | 3.6 |
| 0.2 | 1.0 | 0 | 30 | 20 | 0 | 0 | bal | 43 | 75 | 93 | 99 | 100 | 100 | 85.0 | 0.33 | .72 | 3.6 |
| 0.2 | 1.0 | 0 | 30 | 0 | 5 | 0 | bal | 7 | 12 | 33 | 58 | 80 | 100 | 48.3 | 0.92 | <.20 | <1.0 |
| 0.2 | 1.0 | 0 | 30 | 0 | 10 | 0 | bal | 30 | 52 | 70 | 85 | 97 | 98 | 72.0 | 0.56 | .42 | 2.1 |
| 0.2 | 1.0 | 0 | 30 | 0 | 20 | 0 | bal | 18 | 47 | 66 | 94 | 98 | 100 | 70.5 | 0.58 | .40 | 2.0 |

Analysis of Table 1:

Pyrethrins housefly knockdown in a water-in-oil emulsion is increased approximately 6 times (a.i.) by the addition of 10% vinyl pyrrolidone in a direct spray application. The activity at 10% vinyl pyrrolidone appears to be an optimum, and is associated with the forming of a transparent microemulsion. The potentiating effect of vinyl pyrrolidone is retarded by the presence of the low volatile isopar-L co-solvent that is used to emulsify the standard. Therefore, pyrethrins knockdown in a FIK product can be doubled (a.i.) by replacing the standard 5% isopar-L co-solvent with 5% vinyl pyrrolidone. The potentiation of vinyl pyrrolidone is greater than either methyl pyrrolidone or kerosene without the retardation of isopar-L, but is less effective than methyl pyrrolidone in the standard isopar-L emulsion.

the addition of 10% vinyl pyrrolidone in a space spray application. This increase in knockdown is approximately 60% less than what was demonstrated in Table 1 by a direct spray application of an identical formula. The less efficiency for pyrethrins in this test is contributed to the lesser amount of solvent/cuticle interface that is inherent with a space spray. In a space spray, the flying insect is contacted by discrete droplets that may or may not migrate over the insects' body before penetrating; whereas with a direct spray a continuous film of solvent carrier is immediately deposited over the entire surface of the insect, thus providing more immediate and larger areas of absorption that enhances the rate of toxicant penetration.

All of the pyrrolidone carriers retard pyrethrins knockdown when emulsified with the standard isopar-L co-solvent, confirming that the penetration rate of a volatile solvent carrier is retarded when mixed with a non-volatile co-solvent.

TABLE 2

Housefly Knockdown of Synergized Pyrethrins in a Water-In-Oil Emulsion by a 1 g/216 cu. ft. Space Spray Application Atomized at 45 psi.

| % Concentration In Formula (w/v) | | | | | | | | % Knockdown | | | | KD50 | Equitoxicity | | % Kill |
|---|---|---|---|---|---|---|---|---|---|---|---|---|---|---|---|
| PYR | PB | i-PL | PEN | VP | MP | P | H$_2$O | 3' | 5' | 10' | 15' | Min. | % PYR | Index | 24 hrs. |
| 0.2 | 1.0 | 5 | 30 | 0 | 0 | 0 | bal | 11.7 | 22.7 | 49.7 | 66.3 | 10.3 | 0.2 | 1.0 | 83.3 |
| 0.4 | 1.0 | 5 | 30 | 0 | 0 | 0 | bal | 13.5 | 27.0 | 56.5 | 74.5 | 8.7 | 0.4 | 2.0 | 90.5 |
| 0.8 | 1.0 | 5 | 30 | 0 | 0 | 0 | bal | 25.9 | 45.2 | 70.5 | 86.5 | 5.8 | 0.8 | 4.0 | 99.1 |
| 0.2 | 1.0 | 5 | 30 | 5 | 0 | 0 | bal | 9.5 | 18.5 | 36.0 | 60.5 | 12.5 | <0.2 | <1.0 | 74.4 |
| 0.2 | 1.0 | 5 | 30 | 20 | 0 | 0 | bal | 7.5 | 16.0 | 41.0 | 62.0 | 12.0 | <0.2 | <1.0 | 71.0 |
| 0.2 | 1.0 | 5 | 30 | 0 | 5 | 0 | bal | 11.0 | 19.5 | 39.0 | 59.5 | 12.0 | <0.2 | <1.0 | 71.4 |
| 0.2 | 1.0 | 5 | 30 | 0 | 20 | 0 | bal | 9.5 | 19.0 | 37.0 | 59.5 | 12.0 | <0.2 | <1.0 | 73.9 |
| 0.2 | 1.0 | 5 | 30 | 0 | 0 | 5 | bal | 7.5 | 14.5 | 27.5 | 46.5 | >15.0 | <0.2 | <1.0 | 67.7 |
| 0.2 | 1.0 | 5 | 30 | 0 | 0 | 20 | bal | 10.5 | 19.0 | 39.0 | 55.5 | 12.5 | <0.2 | <1.0 | 73.9 |
| 0.2 | 1.0 | 0 | 30 | 5 | 0 | 0 | bal | 12.8 | 27.5 | 54.0 | 75.8 | 8.7 | 0.40 | 2.0 | 79.2 |
| 0.2 | 1.0 | 0 | 30 | 10 | 0 | 0 | bal | 16.5 | 30.5 | 63.8 | 82.3 | 7.4 | 0.54 | 2.5 | 90.8 |
| 0.2 | 1.0 | 0 | 30 | 20 | 0 | 0 | bal | 14.0 | 30.8 | 61.8 | 82.3 | 7.5 | 0.52 | 2.5 | 91.2 |

Analysis of Table 2:

Pyrethrins housefly knockdown in a water-in-oil emulsion is increased approximately 2.5 times (a.i.) by

TABLE 3

Housefly Knockdown of Synergized Pyrethrins in a Liquid Kerosene Base by a 0.5 g Direct Spray Application Atomized at 10 psi, 18 inch Distance.

| % Concentration In Formula (w/v) | | | | | | | Distance | % Knockdown | | | | | KD50 | Equitoxicity | |
|---|---|---|---|---|---|---|---|---|---|---|---|---|---|---|---|
| PYR | PB | VP | MP | P | KER | ACE | Feet | .25' | .50' | .75' | 1.0' | AVE | Min. | % PYR | Index |
| 0.2 | 1.0 | 0 | 0 | 0 | 80 | bal | 1.0 | 60 | 92 | 100 | 100 | 88.0 | <.25 | — | — |
| 0.4 | 1.0 | 0 | 0 | 0 | 80 | bal | 1.0 | 79 | 97 | 100 | 100 | 94.0 | <.25 | — | — |
| 0.2 | 1.0 | 20 | 0 | 0 | 60 | bal | 1.0 | 96 | 100 | 100 | 100 | 99.0 | <.25 | — | — |
| 0.2 | 1.0 | 80 | 0 | 0 | 0 | bal | 1.0 | 3 | 5 | 15 | 28 | 12.8 | >1.00 | — | — |

TABLE 3-continued

Housefly Knockdown of Synergized Pyrethrins in a
Liquid Kerosene Base by a 0.5 g Direct Spray
Application Atomized at 10 psi, 18 inch Distance.

| % Concentration In Formula (w/v) | | | | | | | Distance | % Knockdown | | | | | KD50 | Equitoxicity | |
|---|---|---|---|---|---|---|---|---|---|---|---|---|---|---|---|
| PYR | PB | VP | MP | P | KER | ACE | Feet | .25' | .50' | .75' | 1.0' | AVE | Min. | % PYR | Index |
| 0.2 | 1.0 | 0 | 20 | 0 | 60 | bal | 1.0 | 75 | 97 | 100 | 100 | 93.0 | <.25 | — | — |
| 0.2 | 1.0 | 0 | 80 | 0 | 0 | bal | 1.0 | 0 | 0 | 4 | 24 | 7.0 | >1.00 | — | — |
| 0.2 | 1.0 | 0 | 0 | 20 | 60 | bal | 1.0 | | non-miscible | | | | — | — | — |
| 0.2 | 1.0 | 0 | 0 | 80 | 0 | bal | 1.0 | 1 | 4 | 15 | 31 | 12.8 | >1.00 | — | — |
| 0.05 | 0.25 | 0 | 0 | 0 | 80 | bal | 1.5 | 6 | 36 | 59 | 80 | 45.3 | 0.60 | .05 | 1.0 |
| 0.10 | 0.50 | 0 | 0 | 0 | 80 | bal | 1.5 | 25 | 50 | 83 | 95 | 63.3 | 0.40 | .10 | 2.0 |
| 0.20 | 1.00 | 0 | 0 | 0 | 80 | bal | 1.5 | 53 | 91 | 99 | 100 | 85.8 | 0.24 | .20 | 4.0 |
| 0.05 | 0.25 | 1 | 0 | 0 | 79 | bal | 1.5 | 13 | 67 | 88 | 94 | 65.5 | 0.42 | .11 | 2.2 |
| 0.05 | 0.25 | 3 | 0 | 0 | 75 | bal | 1.5 | 47 | 90 | 98 | 100 | 83.8 | 0.26 | .18 | 3.5 |
| 0.05 | 0.25 | 5 | 0 | 0 | 75 | bal | 1.5 | 53 | 92 | 100 | 100 | 86.3 | 0.24 | .21 | 4.2 |
| 0.05 | 0.25 | 10 | 0 | 0 | 70 | bal | 1.5 | 60 | 100 | 100 | 100 | 90.0 | 0.23 | .25 | 4.9 |
| 0.05 | 0.25 | 20 | 0 | 0 | 60 | bal | 1.5 | 50 | 100 | 100 | 100 | 87.5 | 0.25 | .22 | 4.4 |
| 0.05 | 0.25 | 40 | 0 | 0 | 40 | bal | 1.5 | 38 | 100 | 100 | 100 | 84.5 | 0.28 | .19 | 3.8 |
| 0.05 | 0.25 | 80 | 0 | 0 | 0 | bal | 1.5 | 2 | 2 | 2 | 2 | 2.0 | >2.0 | <.05 | <1.0 |

Analysis of Table 3:
The test results of Table 3 demonstrate the superiority of the vinyl pyrrolidone/kerosene solution in knocking the fly down within 15 seconds after an 0.5 g direct spray application. All of the pyrrolidones inhibited the knockdown of pyrethrins when used as the only solvent carrier. Maximum knockdown is demonstrated with the 10% vinyl pyrrolidone blend, indicating the optimum concentration for VP in a kerosene base.

Knockdown in this test was deliberately slowed by reducing the concentration of pyrethrins from 0.2 to 0.05%, and by increasing the spray distance from 12 to 18 inches. Under these conditions, 0.05% pyrethrins formulated with 5 to 10% vinyl pyrrolidone appear to have the same housefly knockdown as the 0.2% pyrethrins standard.

TABLE 4

Housefly Knockdown of Synergized Pyrethrins in a
Liquid Kerosene Base by a 1 g/216 cu. ft. Space Spray
Application Atomized at 45 psi.

| % Concentration In Formula (w/v) | | | | | % Knockdown | | | | KD50 | Equitoxicity | | % Kill |
|---|---|---|---|---|---|---|---|---|---|---|---|---|
| PYR | PB | VP | Kerosene | Acetone | 3' | 5' | 10' | 15' | Min. | % PYR | Index | 24 hrs. |
| 0.2 | 1.0 | 0 | 80 | bal | 14 | 24 | 45 | 67 | 10.5 | 0.20 | 1.0 | 78 |
| 0.4 | 1.0 | 0 | 80 | bal | 28 | 33 | 56 | 78 | 8.2 | 0.40 | 2.0 | 95 |
| 0.8 | 1.0 | 0 | 80 | bal | 33 | 46 | 64 | 80 | 7.5 | 0.80 | 4.0 | 98 |
| 0.2 | 1.0 | 5 | 75 | bal | 19 | 27 | 52 | 71 | 9.2 | 0.30 | 1.5 | 65 |
| 0.2 | 1.0 | 10 | 70 | bal | 22 | 32 | 64 | 78 | 7.5 | 0.80 | 4.0 | 68 |
| 0.2 | 1.0 | 20 | 60 | bal | 23 | 37 | 58 | 79 | 7.9 | 0.55 | 2.8 | 78 |
| 0.2 | 1.0 | 80 | 0 | bal | 12 | 21 | 48 | 69 | 10.0 | 0.23 | 1.2 | 79 |

Analysis of Table 4:
Pyrethrins housefly knockdown in a kerosene solution is increased approximately 2.5 times (a.i.) by the addition of 10% vinyl pyrrolidone in a space spray application. This increase in knockdown by a space spray is again approximately 60% less than what is previously demonstrated by a direct spray of an identical formula.

Pyrethrins 24-hour kill is not synergized by the addition of vinyl pyrrolidone, indicating that pyrethrins knockdown and kill are the result of two separate modes-of-action.

TABLE 5

German Cockroach Knockdown of Synergized Pyrethrins
in a Liquid Kerosene Base by a Direct Spray Application
Atomized at 10 psi, 18 inch Distance.

| % Concentration In Formula (w/v) | | | | | | | | % Knockdown | | | | | | | KD50 | Equitoxicity | |
|---|---|---|---|---|---|---|---|---|---|---|---|---|---|---|---|---|---|
| PYR | PB | VP | MP | P | KER | ACE | g. | .25' | .50' | .75' | 1.0' | 1.5' | 3.0' | AVE | Min. | % PYR | Index |
| .05 | .25 | 0 | 0 | 0 | 80 | bal | 1.0 | 5 | 18 | 23 | 38 | 63 | 95 | 40.3 | 1.23 | .05 | 1.0 |
| .10 | .50 | 0 | 0 | 0 | 80 | bal | 1.0 | 12 | 34 | 68 | 84 | 100 | 100 | 66.3 | 0.62 | .10 | 2.0 |
| .20 | 1.00 | 0 | 0 | 0 | 80 | bal | 1.0 | 29 | 59 | 81 | 95 | 100 | 100 | 77.3 | 0.46 | .20 | 4.0 |
| .40 | 1.00 | 0 | 0 | 0 | 80 | bal | 1.0 | 40 | 72 | 100 | 100 | 100 | 100 | 85.3 | 0.33 | .40 | 8.0 |
| .05 | .25 | 1 | 0 | 0 | 79 | bal | 1.0 | 30 | 72 | 96 | 100 | 100 | 100 | 83.0 | 0.36 | .32 | 6.4 |
| .05 | .25 | 5 | 0 | 0 | 75 | bal | 1.0 | 76 | 96 | 100 | 100 | 100 | 100 | 95.3 | <.25 | >.50 | >10.0 |
| .05 | .25 | 10 | 0 | 0 | 70 | bal | 1.0 | 76 | 100 | 100 | 100 | 100 | 100 | 96.0 | <.25 | >.50 | >10.0 |
| .05 | .25 | 20 | 0 | 0 | 60 | bal | 1.0 | 86 | 100 | 100 | 100 | 100 | 100 | 97.7 | <.25 | >.50 | >10.0 |
| .05 | .25 | 80 | 0 | 0 | 0 | bal | 1.0 | 0 | 0 | 2 | 2 | 8 | 30 | 7.0 | >3.00 | <.05 | <1.0 |
| .05 | .25 | 0 | 20 | 0 | 60 | bal | 1.0 | 50 | 86 | 100 | 100 | 100 | 100 | 89.3 | 0.28 | >.50 | >10.0 |
| .05 | .25 | 0 | 80 | 0 | 0 | bal | 1.0 | 8 | 8 | 8 | 16 | 16 | 60 | 19.3 | 2.70 | <.05 | <1.0 |
| .05 | .25 | 0 | 0 | 20 | 60 | bal | 1.0 | | | non-miscible | | | | — | — | — |
| .05 | .25 | 0 | 0 | 80 | 0 | bal | 1.0 | 0 | 0 | 0 | 0 | 2 | 8 | 1.7 | >3.00 | <.05 | <1.0 |
| .05 | .25 | 0 | 0 | 0 | 80 | bal | 0.5 | 1 | 3 | 5 | 7 | 14 | 31 | 10.2 | >3.00 | .05 | 1.0 |
| .10 | .50 | 0 | 0 | 0 | 80 | bal | 0.5 | 10 | 20 | 38 | 48 | 63 | 90 | 44.8 | 1.00 | .10 | 2.0 |
| .20 | 1.00 | 0 | 0 | 0 | 80 | bal | 0.5 | 20 | 46 | 63 | 66 | 76 | 92 | 60.5 | 0.66 | .20 | 4.0 |
| .05 | .25 | 1 | 0 | 0 | 79 | bal | 0.5 | 10 | 23 | 33 | 43 | 59 | 92 | 37.8 | 1.15 | .09 | 1.8 |
| .05 | .25 | 3 | 0 | 0 | 77 | bal | 0.5 | 24 | 38 | 49 | 68 | 78 | 95 | 58.7 | 0.75 | .18 | 3.6 |

TABLE 5-continued

German Cockroach Knockdown of Synergized Pyrethrins in a Liquid Kerosene Base by a Direct Spray Application Atomized at 10 psi, 18 inch Distance.

| % Concentration In Formula (w/v) | | | | | | | | % Knockdown | | | | | | | KD50 | Equitoxicity | |
|---|---|---|---|---|---|---|---|---|---|---|---|---|---|---|---|---|---|
| PYR | PB | VP | MP | P | KER | ACE | g. | .25' | .50' | .75' | 1.0' | 1.5' | 3.0' | AVE | Min. | % PYR | Index |
| .05 | .25 | 5 | 0 | 0 | 75 | bal | 0.5 | 27 | 45 | 63 | 72 | 80 | 97 | 64.0 | 0.54 | E.24 | 4.8 |
| .05 | .25 | 10 | 0 | 0 | 70 | bal | 0.5 | 40 | 55 | 70 | 78 | 83 | 100 | 71.0 | 0.45 | E.33 | 6.6 |
| .05 | .25 | 20 | 0 | 0 | 60 | bal | 0.5 | 38 | 55 | 78 | 85 | 88 | 100 | 74.0 | 0.45 | E.38 | 7.6 |
| .05 | .25 | 40 | 0 | 0 | 40 | bal | 0.5 | 30 | 45 | 50 | 70 | 88 | 100 | 63.8 | 0.64 | E.24 | 4.8 |
| .05 | .25 | 80 | 0 | 0 | 0 | bal | 0.5 | 3 | 3 | 3 | 3 | 5 | 5 | 3.7 | >3.00 | <.05 | <1.0 |

Analysis of Table 5:

Test results again demonstrate the superiority of the vinyl pyrrolidone/kerosene solution in knocking the roach down within 15 seconds after a 1.0 g direct spray application. Pyrethrins knockdown on the roach is potentiated more than 10 times (a.i.) by the addition of 5% vinyl pyrrolidone in the standard kerosene base. Knockdown in this test was deliberately slowed by reducing the amount of spray from 1.0 g to a 0.5 g discharge. The resulting increase in knockdown due to vinyl pyrrolidone is approximately 70% less than the increase demonstrated by the standard 1.0 g spray treatment; again showing that maximum activity with the pyrrolidone is dependent on the amount of solvent that initially interfaces with the insect cuticle.

by the addition of 10% vinyl pyrrolidone. This increase in performance is sufficient to make the normally slow-acting emulsion appear to have the same roach knockdown of a solvent base. The potentiating effect of vinyl pyrrolidone is again retarded when emulsified with the low volatile isopar-L so-solvent. Pyrethrins roach knockdown in an "oil-out" emulsion can be increased at least 5 times (a.i.) by just replacing the standard 5% isopar-L cosolvent with 5% vinyl pyrrolidone. Neither methyl pyrrolidone, 2-pyrrolidone, nor kerosene has the potentiating effect of vinyl pyrrolidone in this experiment.

TABLE 7

German Cockroach Knockdown of Baygon in a Liquid Kerosene Base by a 1 g Direct Spray Application Atomized at 10 psi, 18 inch Distance.

| % Concentration In Formula (w/v) | | | | % Knockdown | | | | | | | KD50 |
|---|---|---|---|---|---|---|---|---|---|---|---|
| Baygon | VP | Kerosene | Acetone | .25' | .50' | .75' | 1.0' | 1.5' | 2.0' | AVE | Min. |
| 1.0 | 0 | 80.0 | bal | 5 | 10 | 10 | 18 | 60 | 83 | 31.0 | 1.40 |
| 1.0 | 2.5 | 77.5 | bal | 3 | 8 | 18 | 45 | 95 | 100 | 44.8 | 1.00 |
| 1.0 | 5.0 | 75.0 | bal | 8 | 18 | 38 | 63 | 85 | 100 | 52.0 | 0.86 |
| 1.0 | 10.0 | 70.0 | bal | 35 | 60 | 73 | 83 | 98 | 100 | 74.8 | 0.40 |
| 1.0 | 20.0 | 60.0 | bal | 33 | 65 | 80 | 85 | 93 | 98 | 75.7 | 0.36 |

Analysis of Table 7:

Baygon's knockdown on the German cockroach is increased approximately 3.5 times (a.i.) by the addition

TABLE 6

German Cockroach Knockdown of Synergized Pyrethrins in a Water-In-Oil Emulsion by a 1 g Direct Spray Application Atomized at 10 psi, 12 inch Distance.

| % Concentration In Formula (w/v) | | | | | | | | % Knockdown | | | | | | | KD50 | Equitoxicity | |
|---|---|---|---|---|---|---|---|---|---|---|---|---|---|---|---|---|---|
| PYR | PB | i-PL | PEN | VP | MP | P | H2O | .25' | .50' | 1.0' | 1.5' | 3.0' | 5.0' | AVE | Min. | % PYR | Index |
| 0.2 | 1.0 | 5 | 30 | 0 | 0 | 0 | bal | 4 | 5 | 10 | 18 | 40 | 59 | 22.7 | 4.2 | 0.2 | 1.0 |
| 0.4 | 1.0 | 5 | 30 | 0 | 0 | 0 | bal | 3 | 9 | 13 | 22 | 53 | 79 | 29.8 | 2.7 | 0.4 | 2.0 |
| 0.8 | 1.0 | 5 | 30 | 0 | 0 | 0 | bal | 4 | 13 | 30 | 43 | 85 | 93 | 44.6 | 1.7 | 0.8 | 4.0 |
| 1.6 | 1.0 | 5 | 30 | 0 | 0 | 0 | bal | 8 | 14 | 39 | 58 | 96 | 100 | 52.5 | 1.2 | 1.6 | 8.0 |
| 0.2 | 1.0 | 5 | 30 | 5 | 0 | 0 | bal | 2 | 7 | 13 | 19 | 63 | 80 | 30.7 | 2.5 | 0.4 | 2.0 |
| 0.2 | 1.0 | 5 | 30 | 20 | 0 | 0 | bal | 26 | 32 | 48 | 62 | 86 | 98 | 58.9 | 1.1 | 2.0 | 10.0 |
| 0.2 | 1.0 | 5 | 30 | 0 | 5 | 0 | bal | 0 | 7 | 10 | 21 | 34 | 65 | 22.8 | 4.0 | 0.2 | 1.0 |
| 0.2 | 1.0 | 5 | 30 | 0 | 20 | 0 | bal | 2 | 4 | 10 | 14 | 36 | 62 | 21.3 | 4.0 | 0.2 | 1.0 |
| 0.2 | 1.0 | 5 | 30 | 0 | 0 | 5 | bal | 0 | 3 | 4 | 11 | 31 | 55 | 17.3 | 4.7 | <0.2 | <1.0 |
| 0.2 | 1.0 | 5 | 30 | 0 | 0 | 20 | bal | 2 | 2 | 4 | 8 | 22 | 52 | 15.0 | 4.9 | <0.2 | <1.0 |
| 0.2 | 1.0 | 0 | 30 | 0 | 0 | 0 | bal | 4 | 9 | 13 | 16 | 33 | 47 | 20.3 | 5.3 | <0.2 | <1.0 |
| 0.2 | 1.0 | 0 | 30 | 5 | 0 | 0 | bal | 16 | 29 | 47 | 49 | 65 | 82 | 48.0 | 1.5 | 1.1 | 5.5 |
| 0.2 | 1.0 | 0 | 30 | 10 | 0 | 0 | bal | 31 | 45 | 74 | 93 | 100 | 100 | 73.8 | 0.6 | >2.0 | >10.0 |
| 0.2 | 1.0 | 0 | 30 | 15 | 0 | 0 | bal | 30 | 63 | 89 | 100 | 100 | 100 | 80.3 | 0.4 | >2.0 | >10.0 |
| 0.2 | 1.0 | 0 | 30 | 20 | 0 | 0 | bal | 37 | 61 | 82 | 90 | 100 | 100 | 78.3 | 0.4 | >2.0 | >10.0 |
| 0.2 | 1.0 | 0 | 30 | 0 | 5 | 0 | bal | 8 | 9 | 12 | 17 | 34 | 48 | 21.3 | 5.4 | <0.2 | <1.0 |
| 0.2 | 1.0 | 0 | 30 | 0 | 10 | 0 | bal | 18 | 24 | 44 | 59 | 84 | 88 | 52.8 | 1.1 | 1.5 | 7.5 |
| 0.2 | 1.0 | 0 | 30 | 0 | 20 | 0 | bal | 8 | 12 | 17 | 23 | 37 | 67 | 27.3 | 3.8 | 0.3 | 1.5 |
| 0.2 | 1.0 | 0 | 30 | 0 | 0 | 5 | bal | 8 | 8 | 13 | 20 | 23 | 33 | 17.5 | >5.0 | <0.2 | <1.0 |
| 0.2 | 1.0 | 0 | 30 | 0 | 0 | 10 | bal | 10 | 10 | 20 | 20 | 33 | 50 | 23.8 | 5.0 | 0.2 | 1.0 |
| 0.2 | 1.0 | 0 | 30 | 0 | 0 | 20 | bal | 15 | 15 | 38 | 43 | 73 | 78 | 43.6 | 1.9 | 0.9 | 4.5 |

Analysis of Table 6:

Pyrethrins German cockroach knockdown in a water-in-oil emulsion is increased more than 10 times (a.i.) of 10% vinyl pyrrolidone in a kerosene direct spray application.

TABLE 8

German Cockroach Knockdown of Baygon in a Water-In-Oil Emulsion by a 1 g Direct Spray Application Atomized at 10 psi, 18 inch Distance.

| % Concentration In Formula (w/v) | | | | | % Knockdown | | | | | KD50 |
|---|---|---|---|---|---|---|---|---|---|---|
| Baygon | MEK | VP | PEN | H$_2$O | 1.0' | 2.0' | 3.0' | 5.0' | AVE | Min. |
| 1.0 | 5 | 0 | 30 | bal | 3 | 5 | 18 | 50 | 19.0 | 5.0 |
| 1.0 | 0 | 5 | 30 | bal | 13 | 18 | 38 | 90 | 39.8 | 3.2 |
| 1.0 | 0 | 10 | 30 | bal | 18 | 35 | 75 | 100 | 57.0 | 2.3 |
| 1.0 | 0 | 15 | 30 | bal | 25 | 48 | 83 | 100 | 64.0 | 2.0 |
| 1.0 | 0 | 20 | 30 | bal | 0 | 10 | 33 | 95 | 34.5 | 3.2 |

Analysis of Table 8:

Baygon's knockdown on the German cockroach is increased approximately 3 times (a.i.) by the addition of 10% N-vinyl pyrrolidone in an oil-out emulsion in a direct spray application.

The experimental results establish that the presence of the N-vinyl 2-pyrrolidone, N-methyl 2-pyrrolidone, and 2-pyrrolidone greatly enhance the knockdown characteristics of an insecticide, with the N-vinyl 2-pyrrolidone being the most effective. As best illustrated by the data contained in Table 3, the 2-pyrrolidones function to provide increased knockdown only in the presence of other solvent carriers. This establishes that the 2-pyrrolidone, therefore, act to increase the penetration of the insecticide into the body of the insect. Further, as best illustrated by the data contained in Table 4, although the knockdown of an insecticide is greatly enhanced by the presence of the 2-pyrrolidones, particularly the N-vinyl 2-pyrrolidone, the kill level is not synergized. This establishes, therefore, that the kill and knockdown characteristics of an insecticide function under different modes. An important and unique feature of the use of the 2-pyrrolidones, and particularly the N-vinyl 2-pyrrolidone, is the ability to obtain a transparent emulsion as best shown from the data contained in Table 6 which has substantially the same knockdown characteristics as a solvent-base insecticide having the same amount of active ingredient. This is unexpected, and is highly significant from the standpoint of cost and ecology.

In accordance with the present invention, the active insecticide can be virtually any of the active insecticidal materials which can be carried in a liquid medium such as the preferred insecticides, in addition to the synergized pyrethrins and as utilized in the examples, are carbamate esters such as; bendiocarb, carbaryl and dioxacarb; organophosphorous esters such as; azamethiphos, chlorpyrifos, diazinon, dichlorvos, malathion, primiphos-methyl and propetamphos; and pyrethroid esters such as; allethrins, cypermethrin, deltamethrin, kadethrin, permethrin, phenothrin, resmethrin and tetramethrin. In the insecticidal composition of this invention, the active insecticide is normally employeed at from about 0.01% to 5% on a weight basis. The optimum amount is from about 0.05% to 1.0% when using a solvent-base system and from about 0.05% to 1.0% when using an emulsion system.

The 2-pyrrolidones can be present in the insecticidal composition of this invention in varying amounts depending in part upon whether the insecticidal composition is an emulsion-base or solvent-base system. Preferably when using an emulsion-base system the pyrrolidones will be utilized in an amount of from about 0.1% to 25% by weight, and optimally at about 1% to 10% based on the volume of liquid medium. When using a solvent-base system, the 2-pyrrolidones will be present in an amount of from about 0.1% to 50%, with the optimum being from about 1.0% to 10% based on the volume of the liquid medium. It is to be understood that the amount of 2-pyrrolidones will vary to some extent based on the active insecticidal agent employed and in the type of system selected. The critical feature is to utilize the 2-pyrrolidones in an amount effective to enhance the knockdown characteristics of the insecticide.

As will be apparent to one skilled in the art, various modifications can be made within the scope of the aforesaid description. Such modifications being within the ability of one skilled in the art form a part of the present invention and are embraced by the appended claims.

It is claimed:

1. An insecticidal composition in liquid medium comprising:
   (a) an active insecticide selected from the group consisting of "pyrethrins, propoxur and pyrethrins and piperonyl butoxide" present in an amount sufficient to kill the housefly and cockroach common to a household;
   (b) a liquid vehicle present in an amount sufficient to solublize, disperse, or emulsify said active insecticide; and
   (c) a knockdown promoter of said housefly and said cockroach consisting of N-vinyl 2-pyrrolidone, said knockdown promoter being present in an amount of 0.1% to 50%, said knockdown promoter acting as a potentiation agent for the insecticide.

2. The insecticidal composition of claim 1 wherein said composition is a water-out emulsion and said knockdown promoter is present in an amount of from 0.1% to 25% based on the volume of the liquid vehicle of the emulsion.

3. The insecticidal composition of claim 1 wherein said composition is an oil-out emulsion and said knockdown promotor is present in an amount of from 0.1% to 25% based on the volume of the liquid vehicle of the emulsion.

4. The insecticidal composition of claim 1 wherein said active insecticide is a synergistic combination of pyrethrins and piperonyl butoxide.

5. A method of combatting houseflies and cockroaches common to a household which comprises applying to said houseflies and cockroaches or the locus thereof an insecticidally effective amount of the composition of claims 1, 2, 3 or 4.

* * * * *